(12) United States Patent
Hara et al.

(10) Patent No.: US 7,432,085 B2
(45) Date of Patent: *Oct. 7, 2008

(54) METHOD FOR PRODUCING L-AMINO ACID

(75) Inventors: Yoshihiko Hara, Kawasaki (JP); Hiroshi Izui, Kawasaki (JP); Takahiro Asano, Kawasaki (JP); Yasuyuki Watanabe, Kawasaki (JP); Tsuyoshi Nakamatsu, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 256 days.

This patent is subject to a terminal disclaimer.

(21) Appl. No.: 11/281,495

(22) Filed: Nov. 18, 2005

(65) Prior Publication Data

US 2006/0115878 A1 Jun. 1, 2006

Related U.S. Application Data

(63) Continuation of application No. 10/396,488, filed on Mar. 26, 2003, now Pat. No. 7,037,690.

(30) Foreign Application Priority Data

Mar. 27, 2002 (JP) ............................. 2002-88668

(51) Int. Cl.
*C12P 13/04* (2006.01)
*C12P 13/06* (2006.01)
*C12P 13/16* (2006.01)
*C12P 13/20* (2006.01)
*C12P 13/24* (2006.01)

(52) U.S. Cl. ............... 435/106; 435/107; 435/108; 435/109; 435/110; 435/113; 435/114; 435/115; 435/116; 536/23.1; 536/23.2

(58) Field of Classification Search ............ 435/106, 435/107–110, 113–116, 194, 252.33; 536/23.1, 536/23.2

See application file for complete search history.

(56) References Cited

U.S. PATENT DOCUMENTS

| 5,786,186 | A * | 7/1998 | Lancashire et al. ........ 435/161 |
| 6,331,419 | B1 | 12/2001 | Moriya et al. |
| 6,596,517 | B2 | 7/2003 | Izui et al. |
| 7,037,690 | B2 * | 5/2006 | Hara et al. ................ 435/106 |
| 7,217,543 | B2 * | 5/2007 | Gunji et al. ............... 435/106 |

FOREIGN PATENT DOCUMENTS

| DE | 101 35 051 | 2/2003 |
| EP | 0 733 710 | 9/1996 |
| EP | 0 952 221 | 10/1999 |
| EP | 0 999 282 | 5/2000 |
| EP | 1 078 989 | 2/2001 |
| WO | WO 01/02542 | 1/2001 |
| WO | WO 01/02543 | 1/2001 |
| WO | WO 01/48146 | 7/2001 |

OTHER PUBLICATIONS

J.M. Smith, et al., NCBI, GenBank Accession L20897, pp. 1-3, "Purine and One-Carbon Metabolism in *Escherichia coli* K12: DNA Sequence of a Second Gar Transformylase", Jul. 26, 1993.
T. Conway, et al., NCBI, GenBank Accession X58364, pp. 1-2, "Cloning Characterization and Expression of the *Zymononas mobilis* EDA Gene That Encodes 2-Keto-3-Deoxy-6-Phosphongluconate Aldolase of the Entner-Doudoroff Pathway", Dec. 4, 1998.
W.O. Barnell, et al., NCBI, GenBank Accession M60615, M37982, pp. 1-4, "Sequence and Genetic Organization of a *Zymomonas mobilis* Gene Cluster That Encodes Several Enzymes of Glucose Metabolism", Apr. 26, 1993.
N. Peekhaus, et al., Journal of Bacteriology, vol. 180, No. 14, pp. 3495-3502, XP-002262000, "What's for Dinner?: Entner-Doudoroff Metabolism in *Escherichia coli*", Jul. 1998.
K. Ueda, Fermentation Advances, pp. 43-62, XP-002107644, "Some Fundamental Problems of Continuous L-Glutamic Acid Fermentation", 1969.
Egan, S. E., et al., "Molecular Characterization of the Entner-Doudoroff Pathway in *Escherichia coli*: Sequence Analysis and Localization of Promoters for the edd-eda Operon," Journal of Bacteriology, Jul. 1992, vol. 174, No. 14, pp. 4638-4646.
Conway, T., et al., "Locations of the zwf, edd, and eda Genes on the *Escherichia coli* Physical Map," Journal of Bacteriology, vol. 173, No. 17, Sep. 1991, pp. 5247-5248.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

In a method for producing an L-amino acid by culturing a microorganism having an ability to produce an L-amino acid in a medium to produce and accumulate the L-amino acid in the medium and collecting the L-amino acid from the medium, a Gram-negative bacterium having the Entner-Doudoroff pathway and modified so that 6-phosphogluconate dehydratase activity or 2-keto-3-deoxy-6-phosphogluconate aldolase activity, or activities of the both are enhanced is used as the microorganism.

10 Claims, 2 Drawing Sheets

METHOD FOR PRODUCING L-AMINO ACID

CROSS-REFERENCE TO RELATED APPLICATIONS

The present application is a continuation of U.S. Ser. No. 10/396,488, filed on Mar. 26, 2003, which claims priority to JP 2002-088668, filed on Mar. 27, 2002.

FIELD OF THE INVENTION

The present invention relates to methods for producing L-amino acids and bacteria used for the same. More precisely, the present invention relates to bacteria having an improved ability to produce L-amino acid and methods for producing L-amino acids using the same.

DESCRIPTION OF THE RELATED ART

Conventionally, L-amino acids such as L-glutamic acid are mainly produced by fermentation utilizing so-called coryneform bacteria belonging to the genus *Brevibacterium*, *Cozynebacterium* or *Microbacterium* ("Amino Acid Fermentation", Gakkai Shuppan Center, pp. 195-215, 1986). Further, microorganisms of the genus *Bacillus, Streptomyces, Penicillium* (U.S. Pat. No. 3,220,929), *Pseudomonas, Arthrobacter, Serratia, Aerobacter, Candida* (U.S. Pat. No. 3,563,857), *Escherichia* (Japanese Patent Laid-open Publication (Kokai) No. 5-244970) or the like can be also utilized in the production of L-amino acids. Further, microorganisms belonging to the genus *Enterobacter* (EP1078989A2), *Klebsiella, Erwinia* or *Pantoea* (Japanese Patent Laid-open Publication No. 2000-106869) can be also utilized in the production of L-amino acids such as L-glutamic acid.

Further, there have been disclosed various techniques for increasing an L-amino acid producing ability by enhancing enzymes involved in the biosynthesis of L-amino acids by recombinant DNA techniques. For example, there have been disclosed a method for producing L-glutamic acid by utilizing a bacterium belonging to the genus *Enterobacter* or *Klebsiella* into which a citrate synthase gene is introduced (EP0999282A2), and a method for producing L-glutamic acid by utilizing a bacterium belonging to the genus *Enterobacter* into which genes coding for citrate synthase, phosphoenolpyruvate carboxylase and glutamate dehydrogenase are introduced (EP 1 078 989 A2).

Further, there are also known techniques for enhancing L-amino acid producing ability by introducing genes coding for glycolytic enzymes such as glucose-6-phosphate isomerase (WO 01/02542 A1), fructose phosphotransferase (WO 01/48146 A1) and enolase (WO 01/02543 A1).

Meanwhile, many Gram-negative bacteria including enterobacteria have the Entner-Doudoroff pathway as one of glucose metabolic pathways. This pathway involves 6-phosphogluconate dehydratase (abbreviated as "EDD" hereinafter), which catalyzes a reaction to produce 2-keto-3-deoxy-6-phosphogluconate from 6-phosphogluconic acid, and 2-keto-3-deoxy-6-phosphogluconate aldolase (abbreviated as "EDA" hereinafter), which cleaves 2-keto-3-deoxy-6-phosphogluconate to produce glyceraldehyde-3-phosphate and pyruvic acid. Genes coding for EDD and EDA have been cloned from *Escherichia coli, Zymomonas mobilis* and so forth, and their nucleotide sequences have been reported. The nucleotide sequences of the gene coding for EDD (edd) and the gene coding for EDA (eda) of *Escherichia coli* are registered as GenBank accession number L20897. Further, the nucleotide sequence of the eda gene of *Zymomonas mobilis* is registered as GenBank accession number X58364, and the nucleotide sequence of the edd gene thereof is registered as GenBank accession number M60615 M37982 in the database.

However, relationship between the Entner-Doudoroff pathway and productivity of L-amino acids are unknown.

SUMMARY OF THE INVENTION

An object of the present invention is to provide a technique for improving productivity of L-amino acids in bacteria from a viewpoint different from known techniques.

The inventors of the present invention focused their attention on the Entner-Doudoroff pathway possessed by Gram-negative bacteria. Among metabolic pathways from saccharides to L-amino acids such as L-glutamic acid, carbon dioxide is produced by a reaction for producing ribulose-5-phosphate from 6-phosphogluconic acids by 6-phosphogluconate dehydrogenase. In bacterial strains having a large carbon inflow into the pentose phosphate pathway, in particular, a large amount of carbon dioxide should also be released by the above-mentioned reaction. Therefore, they considered that an ability to produce an L-amino acid such as L-glutamic acid could be improved by avoiding the inflow into the pentose phosphate pathway.

Two of methods for reducing the inflow of carbon into the pentose phosphate pathway are conceived: (1) eliminating or reducing an activity of glucose-6-phosphate dehydrogenase or 6-phosphogluconate dehydrogenase; and (2) enhancing the Entner-Doudoroff pathway. Both of the methods can be expected to have an effect of bypassing the pentose phosphate pathway. However, in the case of (2), it is considered that, since carbon distribution with respect to the pentose phosphate pathway can be changed by regulating the activities of EDD and EDA, a derivative of an intermediate substance in the pentose phosphate pathway such as nucleic acid can also be supplied. Further, as a result of various investigations, they found that an ability of bacteria to produce L-amino acids can be improved by enhancing the Entner-Doudoroff pathway, and thus accomplished the present invention.

That is, the present invention provides the followings.

(1) A method for producing an L-amino acid comprising culturing a microorganism having an ability to produce an L-amino acid in a medium to produce and accumulate the L-amino acid in the medium and collecting the L-amino acid from the medium, wherein the microorganism is a Gram-negative bacterium having the Entner-Doudoroff pathway and which has been modified so that 6-phosphogluconate dehydratase activity or 2-keto-3-deoxy-6-phosphogluconate aldolase activity, or activities of the both are enhanced, and the L-amino acid is selected from L-amino acids produced by a biosynthetic pathway utilizing pyruvic acid as an intermediate.

(2) The method according to (1), wherein the bacterium is an enterobacterium.

(3) The method according to (2), wherein the bacterium is belonging to the genus *Enterobacter*.

(4) The method according to any one of (1) to (3), wherein the 6-phosphogluconate dehydratase activity or 2-keto-3-deoxy-6-phosphogluconate aldolase activity is enhanced by increasing copy number of a gene coding for 6-phosphogluconate dehydratase or 2-keto-3-deoxy-6-phosphogluconate aldolase or modifying an expression regulatory sequence of the gene so that expression of the gene is enhanced in a cell of the bacterium.

(5) The method according to (1), wherein the L-amino acid is L-glutamic acid or an L-amino acid produced by a biosynthetic pathway utilizing L-glutamic acid as an intermediate or an amino group donor.

(6) The method according to any one of (1) to (5), wherein the L-amino acid is selected from L-glutamic acid, L-arginine, L-glutamine, L-proline, L-leucine, L-isoleucine, L-valine and L-alanine.

(7) The method according to (6), wherein the L-amino acid is L-glutamic acid.

According to the present invention, by increasing activity of Entner-Doudoroff pathway, an ability of a microorganism having the pathway to produce L-amino acid can be improved.

DETAILED EXPLANATION OF THE INVENTION

Figure 1:
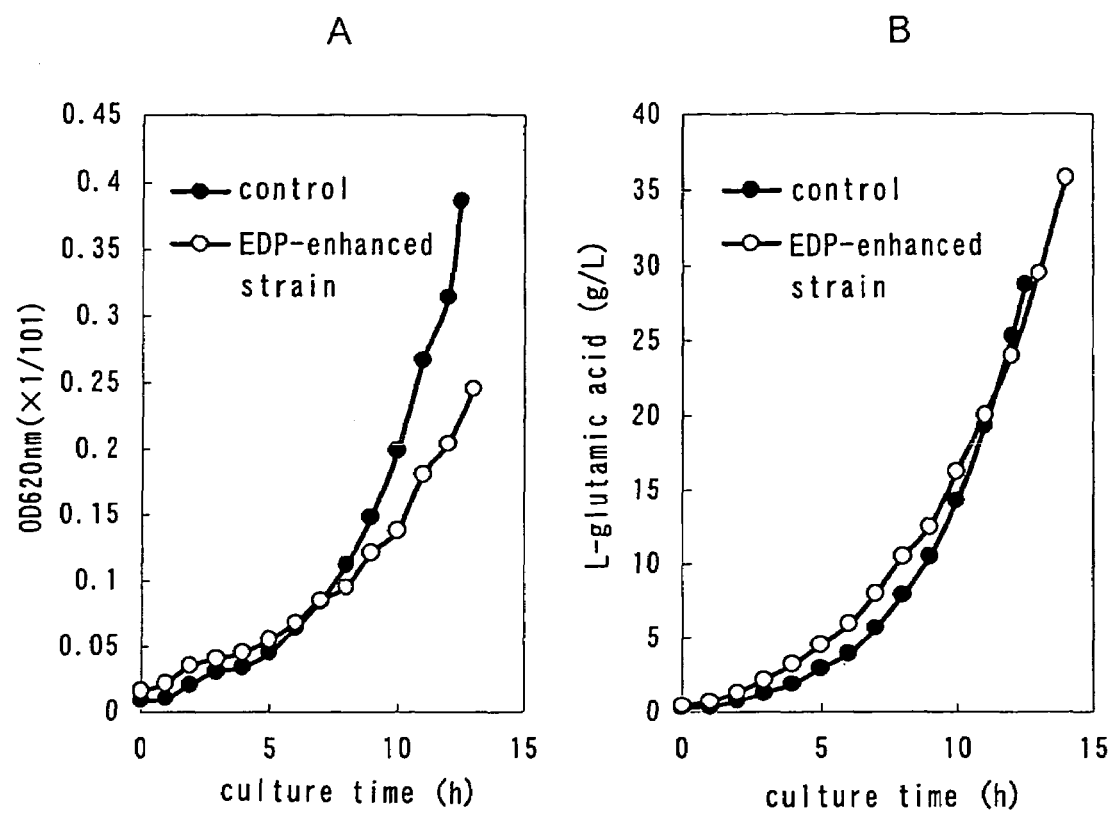
FIG. 1 shows growth of a strain in which the edd gene and eda gene are enhanced (A) and the amount of produced L-glutamic acid (B).

Hereafter, the present invention will be explained in detail.

<1> Bacterium of the Present Invention

The Gram-negative bacterium used for the present invention is a Gram-negative bacterium having an ability to produce an L-amino acid and the Entner-Doudoroff pathway.

The term "an ability to produce an L-amino acid" used in the present invention means an ability to accumulate the L-amino acid in a medium when the bacterium of the present invention is cultured in the medium. This ability to produce an L-amino acid may be a property of a wild strain of the Gram-negative bacterium or a property imparted or enhanced by breeding. L-amino acids to which the present invention can be applied are L-amino acids produced by a biosynthetic pathway utilizing pyruvic acid as an intermediate. Specific examples thereof include L-glutamic acid, L-arginine, L-glutamine, L-proline, L-leucine, L-isoleucine, L-valine, L-alanine and so forth.

As shown in the examples described later, a bacterium having the Entner-Doudoroff pathway enhanced by increasing activities of EDD and EDA showed increased production of acetoin and 2,3-butanediol. Since 2,3-butanediol is produced from acetoin, and acetoin is produced from pyruvic acid, increase in production of acetoin and 2,3-butanediol indicates an increase in the amount of supplied pyruvic acid. Therefore, the bacterium having the enhanced Entner-Doudoroff pathway is expected to have an increased ability to produce an L-amino acid produced by a biosynthetic pathway utilizing pyruvic acid as an intermediate.

Specific examples of the Gram-negative bacteria having the Entner-Doudoroff pathway include bacteria belonging to the genera *Enterobacter, Klebsiella, Serratia, Erwinia* or *Pantoea, Escherichia, Pseudomonas, Arthrobacter,* and *Aerobacter* and so forth. Whether a bacterium has the Entner-Doudoroff pathway or not can be determined by, for example, mixing a cell-disrupted suspension with glyceraldehyde-3-phosphate dehydrogenase, 6-phosphogluconic acid and acetylpyridine adenine dinucleotide and detecting glyceraldehyde-3-phosphate produced from 6-phosphogluconic acid as a substrate by measuring increase of absorbance at 365 nm. A bacterium that is confirmed to produce glyceraldehyde-3-phosphate has the Entner-Doudoroff pathway.

Bacteria used for the present invention may be suitably selected depending on the type of target L-amino acid. Bacteria suitable for the production of L-glutamic acid are exemplified below. However, the scope of the present invention is not limited to these examples.

Specific examples of the *Enterobacter* bacteria include following bacteria.

*Enterobacter agglomerans*
*Enterobacter aerogenes*
*Enterobacter amnigenus*
*Enterobacter asburiae*
*Enterobacter cloacae*
*Enterobacter dissolvens*
*Enterobacter gergoviae*
*Enterobacter hormaechei*
*Enterobacter intermedius*
*Enterobacter nimipressuralis*
*Enterobacter sakazakii*
*Enterobacter taylorae*

More preferred are the following bacterial strains.
*Enterobacter agglomerans* ATCC 12287
*Enterobacter agglomerans* AJ13355
*Enterobacter agglomerans* AJ13356
*Enterobacter agglomerans* AJ13601

*Enterobacter agglomerans* AJ13355 and AJ13556 were deposited at National Institute of Bioscience and Human-Technology, Agency of Industrial Science and Technology (presently, the independent administrative corporation, International Patent Organism Depositary, National Institute of Advanced Industrial Science and Technology, Address: Chuo Dai-6, 1-1 Higashi 1-Chome, Tsukuba-shi, Ibaraki-ken, Japan, postal code: 305-5466) on Feb. 19, 1998 and received accession numbers of FERM P-16644 and FERM P-16645, respectively. Then, the depositions were converted into international depositions under the provisions of the Budapest Treaty on Jan. 11, 1999 and received accession numbers of FERM BP-6614 and FERM BP-6615. *Enterobacter agglomerans* AJ13601 was deposited at National Institute of Bioscience and Human-Technology, Agency of Bioscience and Human Technology on Aug. 18, 1999 and received an accession number of FERM P-17516. Then, the deposition was converted into an international deposition under the provisions of the Budapest Treaty on Jul. 6, 2000 and received an accession number of FERM BP-7207. *Enterobacter agglomerans* ATCC 1228.7 can be distributed from ATCC (American Type Culture Collection, 10801 University Boulevard, Manassas, Va. 20110-2209, U.S.A.).

Examples of bacteria belonging to the genus *Klebsiella* include the following bacteria.
*Klebsiella planticola*
*Klebsiella terrigena*

More preferred is *Klebsiella planticola* AJ13399. *Klebsiella planticola* AJ13399 was deposited at National Institute of Bioscience and Human-Technology, Agency of Bioscience and Human Technology (presently, the independent administrative corporation, International Patent Organism Depositary, National Institute of Advanced Industrial Science and Technology) on Feb. 19, 1998 and received an accession number of FERM P-16646. Then, the deposition was converted into an international deposition under the provisions of the Budapest Treaty on Jan. 11, 1999 and received an accession number of FERM BP-6616.

The *Klebsiella planticola* AJ13399 strain is a strain isolated from soil in Sapporo-shi, Hokkaido.

Examples of the microorganisms belonging to the genus *Serratia* used for the present invention include the followings.

*Serraatia liquefacience*
  *Serratia entomophila*
  *Serratia ficaria*
  *Serratia fonticola*
  *Serratia grimesii*
  *Serratia proteamaculans*
  *Serratia odorifera*
  *Serratia plymuthica*
  *Serratia rubidaea*

More preferred are the following bacterial strains.

*Serratia liquefacience* ATCC 14460

*Serratia liquefacience* ATCC 14460 can be distributed from ATCC.

Examples of the microorganisms belonging to the genus *Erwinia* used for the present invention include the followings.

*Erwinia herbicola* (presently classified as *Pantoea agglomerans*)
  *Erwinia ananas*
  *Erwinia cacticida*
  *Erwinia chrysanthemi*
  *Erwinia mallotivora*
  *Erwinia persicinus*
  *Erwinia psidii*
  *Erwinia quercina*
  *Erwinia rhapontici*
  *Erwinia rubrifaciens*
  *Erwinia salicis*
  *Erwinia uredovora*

More preferred is *Erwinia herbicola* IAM1595 (*Pantoea agglomerans* AJ2666). The *Erwinia herbicola* IAM1595 can be distributed from Institute of Molecular and Cellular Biosciences, the University of Tokyo.

*Erwinia herbicola* is not mentioned in Bergey's Manual of Determinative Bacteriology, 9th Ed., and the microorganism that has been classified as *Erwinia herbicola* is classified as *Pantoea agglomerans*. Thus, microorganisms belonging to the genus *Erwinia* and microorganisms belonging to the genus *Pantoea* are closely related to each other. Therefore, microorganisms belonging to the genus *Pantoea* can similarly be used as microorganisms belonging to the genus *Erwinia*. As such microorganisms belonging to the genus *Pantoea*, there can be mentioned *Pantoea agglomerans, Pantoea dispersa* and *Pantoea ananas*. *Erwinia herbicola* IAM1595 was designated as *Pantoea agglomerans* AJ2666, deposited at National Institute of Bioscience and Human-Technology, Agency of Bioscience and Human Technology (presently, International Patent Organism Depositary, National Institute of Advanced Industrial Science and Technology) as an international deposition under the provisions of the Budapest Treaty on Feb. 25, 1999 and received an accession number of FERM BP-6660.

Examples of the microorganisms belonging to the genus *Escherichia* used for the present invention include *Escherichia coli*.

More preferred is *Escherichia coli* having valine resistance, and specific examples are the following strains.

*Escherichia coli* K-12 (ATCC 10798)
  *Escherichia coli* W (ATCC 9637)

*Escherichia coli* K-12 (ATCC 10798) and *Escherichia coli* W (ATCC 9637) can be distributed from ATCC.

The Gram-negative bacterium of the present invention is a Gram-negative bacterium which has an ability to produce an L-amino acid and the aforementioned Entner-Doudoroff pathway and which has been modified so that EDD or EDA activity or both of the activities are enhanced. The bacterium of the present invention is preferably a Gram-negative bacterium which has been modified so that both activities of EDD and EDA are enhanced.

The expression "modified so that EDD or EDA activity is enhanced" means that EDD or EDA activity per cell is made higher than that of a wild type bacterium. For example, those in which the number of EDD or EDA molecules per cell is increased, those in which specific activity of EDD or EDA per EDD or EDA molecule is increased and so forth can be mentioned. Further, the wild type bacterium to be compared is a bacterium that has not been subjected to any manipulation for enhancing EDD or EDA activity.

Enhancement of the EDD and/or EDA activity in a bacterium is achieved by increasing copy number of a gene coding for EDD and/or EDA. For example, recombinant DNA can be prepared by ligating a gene fragment coding for EDD and/or EDA with a vector functioning in a target bacterium, preferably a multi-copy type vector, and can be introduced into the bacterium to transform it. When both of activities of EDD and EDA are enhanced, the gene fragment coding for EDD and the gene fragment coding for EDA may be separately incorporated-into different vectors, but they are preferably incorporated into the same vector. The recombinant DNA may be introduced into a bacterium having an L-amino acid producing ability, alternatively the recombinant DNA may be introduced into a wild-type bacterium to obtain a transformant strain, and then the transformant strain may be imparted with the L-amino acid producing ability.

As the gene coding for EDD and the gene coding for EDA, any of genes derived from Gram-negative bacteria having the Entner-Doudoroff pathway can be used. Specifically, genes derived from *Esherichia* bacteria can be mentioned. It has been reported that the gene coding for EDD (edd) and gene coding for EdzA (eda) derived from *Escherichia coli* form an operon (J. Bacteriol., 174 (14): 4638-46, July 1992). Hereinafter, the gene coding for EDD is referred to as edd, and the gene coding for EDA is referred to as eda. Further, genes of bacteria of the genus *Zymomonas* have also been reported, and the edd gene and eda gene can be obtained by PCR (Polymerase Chain Reaction, refer to White, T. J. et al., Trends Genet. 5, 185 (1989)) using primers prepared based on the sequences of those genes or hybridization using a probe prepared based on the aforementioned gene sequences. For example, an operon fragment containing the edd gene and eda gene of *Escherichia coli* can be obtained by PCR using primers edd-F (SEQ ID NO: 1) and eda-R (SEQ ID NO: 2) described later. The edd gene and eda gene of other microorganisms can be similarly obtained. The hybridization condition is exemplified by a condition under which washing is performed at a salt concentration corresponding to 1×SSC, 0.1% SDS, preferably 0.1×SSC, 0.1% SDS, at 60° C.

Further, the edd gene and eda gene used for the present invention are not limited to wild-type genes, and they may be mutants or artificially modified genes coding for gene products including substitution, deletion, insertion, addition or the like of one or several amino acids at one or-more sites so long as the functions of the encoded EDD and EDA are not degraded. Although the number of "several" amino acids referred to herein differs depending on the position or type of amino acid residues in a three-dimensional structure of a protein, but it may be specifically 2 to 60, preferably, 2 to 40, more preferably 2 to 20. Further, as DNA coding for a protein substantially identical to the aforementioned EDD and/or EDA, there can be mentioned DNA hybridizable with nucleotide sequences of a known edd or eda gene (for example, GenBank accession L20897, X58364, M60615 M37982) or a probe that can be produced from these nucleotide sequences under a stringent condition and codes for a protein having an activity similar to that of EDD or EDA. The "stringent condition" referred to herein is a condition under which a so-called specific hybrid is formed, and a non-specific hybrid is not formed. It is difficult to clearly express this condition by using numerical values. However, for example, the stringent condition includes a condition under which DNAs having high homology, for example, DNAs having homology of 50% or more, are hybridized with each other, but DNAs having homology lower than the above are not hybridized with each other. Alternatively, the stringent condition is exemplified by a condition under which DNAs are hybridized with each other at a salt concentration corresponding to an ordinary washing condition of Southern hybridization, i.e., 1×SSC, 0.1% SDS, preferably 0.1×SSC, 0.1% SDS, at 60° C.

Chromosomal DNA can be prepared from a bacterium as a DNA donor by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992) or the like.

If a recombinant DNA is prepared by ligating the edd gene and/or eda gene amplified by PCR with vector DNA autonomously replicable in a cell of *Escherichia coli* or the like and introduced into *Escherichia coli*, subsequent operations become easier. Examples of the vector autonomously replicable in the *Escherichia coli* cell include pMW219, pSTV28, pUC19, pUC18, pHSG299, pHSG399, pHSG398, RSF1010, pBR322, pACYC184 and so forth.

To introduce the recombinant DNA prepared as described above into a Gram-negative bacterium, transformation methods that have been reported so far can be employed. For example, there can be mentioned the method of D. A. Morrison (Methods in Enzymology, 68, 326 (1979)), a method of treating recipient cells with calcium chloride so as to increase permeability for DNA (Mandel, M. and Higa, A., J. Mol. Biol., 53, 159 (1970)), an electroporation method (Miller J. H., "A Short Course in Bacterial Genetics; Handbook", Cold Spring Harbor Laboratory Press, U.S.A., p. 279, 1992) and so forth.

The copy number of the edd gene and/or eda gene can also be increased by allowing multiple copies of these genes to exist in chromosomal DNA of a bacterium. To introduce multiple copies of the edd gene and/or eda gene into chromosomal DNA of a bacterium, homologous recombination is carried out by using a sequence whose multiple copies exist in the chromosomal DNA as a target. As sequences whose multiple copies exist in the chromosomal DNA, repetitive DNA or inverted repeat existing at an end of transposable element can be used. Further, as disclosed in Japanese Patent Laid-open Publication No. 2-109985, it is also possible to incorporate the edd gene and/or eda gene into a transposon, and allow it to be transferred to introduce multiple copies of the genes into the chromosomal DNA.

The enhancement of EDD and/or EDA activities can also be attained, besides being based on the aforementioned gene amplification, by replacing an expression regulatory sequence such as a promoter of the edd gene and/or eda gene in chromosomal DNA or plasmid with a stronger one. For example, lac promoter, trp promoter, trc promoter and so forth are known as strong promoters. Further, as disclosed in International Patent Publication WO00/18935, by introducing a substitution of several nucleotides into the promoter region of the edd gene and/or eda gene, the promoter can be modified so as to become a stronger promoter. Substitution or modification of these promoters enhances expression of the edd gene and/or eda gene, and thus activities of EDD and/or EDA are enhanced. Modification of these expression regulatory sequences can be combined with the increase of copy number of the edd gene and/or eda gene.

Enhancement of the activities of EDD and EDA can be confirmed by mixing a cell-disrupted suspension with glyceraldehyde-3-phosphate dehydrogenase and 6-phosphogluconic acid and measuring glyceraldehyde-3-phosphate produced from 6-phosphogluconic acid as a substrate. In this reaction, EDD activity can be measured by quantifying 6-phosphogluconic acid remaining after the reaction by using 6-phosphogluconate dehydrogenase, or quantifying pyruvic acid produced in the presence of excessive 2-keto-3-deoxy-6-phosphogluconate aldolase using lactate dehydrogenase. The 6-phosphogluconic acid or pyruvic acid can be quantified as increase of NADH in the dehydrogenase reaction. Further, EDA activity can also be measured by detecting pyruvic acid produced from 2-keto-3-deoxy-6-phosphogluconate as a substrate by using lactate dehydrogenase.

In the Gram-negative bacterium of the present invention, activity of enzyme catalyzing an L-amino acid biosynthesis other than. EDD and EDA may be enhanced so long as the effect of enhancing activities of EDD and EDA is not degraded.

For example, when a target L-amino acid is L-glutamic acid, examples of such an enzyme include glutamate dehydrogenase (also referred to as "GDH" hereinafter), glutamine synthetase, glutamate synthase, isocitrate dehydrogenase, aconitate hydratase, citrate synthase (also referred to as "CS" hereinafter), phosphoenolpyruvate carboxylase (also referred to as "PEPC" hereinafter), phosphoenolpyruvate synthase, pyruvate dehydrogenase, pyruvate kinase, pyruvate carboxylase, enolase, phosphoglyceromutase, phosphoglycerate kinase, glyceraldehyde-3-phosphate dehydrogenase, triose phosphate isomerase, fructose bisphosphate aldolase, phosphofructokinase, glucose phosphate isomerase and so forth. When a bacterium used for the production of L-glutamic acid is an *Enterobacter* bacterium, any one to three kinds of CS, PEPC and GDH are preferred among the aforementioned enzymes. Further, it is preferred that activities of the three kinds of enzymes, CS, PEPC, and GDH, are all enhanced. In particular, CS of *Brevibacterium lactofermentum* is preferred because it does not suffer from inhibition by α-ketoglutaric acid, L-glutamic acid and NADH.

As organisms that can be supply sources of the gene coding for CS (gltA), the gene coding for PEPC (ppc) and the gene coding for GDH (gdhA), any organisms can be used so long as they have activities of CS, PEPC and GDH. In particular, bacteria, which are prokaryotes, for example, bacteria belonging to the genus *Enterobacter, Klebsiella, Erwinia, Pantoea, Serratia, Escherichia, Corynebacterium, Brevibacterium* or *Bacillus* are preferred. Specific examples thereof include *Escherichia coli, Brevibacterium lactofermentum* and so forth. The gltA gene, ppc gene and gdhA gene can be obtained from chromosomal DNA of the aforementioned microorganisms.

The gltA gene, ppc gene and gdhA gene can be obtained by using a mutant deficient in CS, PEPC or GDH activity and isolating a DNA fragment complementing its auxotrophy from the chromosomal DNA of the aforementioned microorganisms. Further, since nucleotide sequences of these genes of *Escherichia* bacteria and these genes of *Corynebacterium* bacteria have already been elucidated (Biochemistry, 22: 5243-5249, 1983; J. Biochem., 95: 909-916, 1984; Gene, 27: 193-199, 1984; Microbiology, 140: 1817-1828, 1994; Mol. Gen. Genet., 218, 330-339, 1989; Molecular Microbiology, 6: 317-326, 1992), they can be obtained by synthesizing primers based on the respective nucleotide sequences, and performing PCR using chromosomal DNA as a template. Introduction of these genes into a Gram-negative bacterium such as *Enterobacter* bacteria is described in EP 0 670 370 A2, U.S. Pat. No. 6,197,559, EP 0 999 282 A2 and EP 1 078 989 A2 in detail.

The activities of CS, PEPC and GDH as well as the aforementioned other enzymatic activities can be enhanced in the same manner as the enhancement of the EDD and EDA activities mentioned above.

Further, in the bacterium of the present invention, an enzymatic activity for catalyzing a reaction for producing another compound by branching from a biosynthetic pathway of a target L-amino acid may be reduced or eliminated so long as the effect of enhancement of the EDD and/or EDA activities is not degraded. For example, when the target L-amino acid is L-glutamic acid, examples of such an enzyme include α-ketoglutarate dehydrogenase (also referred to as "αKGDH" hereinafter), isocitrate lyase, phosphate acetyltransferase, acetate kinase, acetohydroxy acid synthase, acetolactate synthase, formate acetyltransferase, lactate dehydrogenase, L-glutamate decarboxylase, 1-pyrroline dehydrogenase and so forth.

To reduce or eliminate activities of the aforementioned enzymes, a method of treating a microorganism with ultraviolet ray irradiation or a mutagenesis agent used in a usual mutation treatment such as N-methyl-N'-nitro-N-nitrosoguanidine (NTG) or nitrous acid and selecting a mutant strain in which a target enzymatic activity is reduced, a gene disruption method utilizing gene substitution based on homologous recombination, or the like can be employed. The gene disruption of the gene coding for αKGDH is described in U.S. Pat. No. 5,977,331.

When genes other than the edd gene and eda gene are introduced upon the construction of the bacterium of the present invention, it is preferred to use fewer kinds of vectors. That is, a vector usually has a marker gene, and an agent corresponding to the marker gene or the like needs to be added to a medium. Therefore, if many kinds of vectors are used, a large number of agents must be added to the medium. This may result in poor growth of bacteria. Therefore, it is usually preferable to use a fewer kinds of vectors. It is preferable to use two or less kinds, more preferably of one kind, of vectors or vector.

Further, when two or more kinds of vectors each having a different copy number are used, it is preferable to determine the distribution of the genes between a vector of a high copy number and a vector of a low copy number depending on the kinds of the genes to be introduced.

For the operations of isolation of a gene, introduction of a gene into a host bacterium, gene disruption and so forth, usual methods well known to those skilled in the art can be employed as the methods for preparation of chromosomal DNA, construction of chromosomal DNA library, hybridization, PCR, preparation of plasmid DNA, digestion and ligation of DNA, transformation, design of oligonucleotides used as primers and so forth. These methods are described in Sambrook J., Fritsch E. F., and Maniatis T., "Molecular Cloning A Laboratory Manual, Second Edition", Cold Spring Harbor Laboratory Press, (1989) and so forth.

<2> Production of L-amino Acid Using Bacterium of the Present Invention

An L-amino acid can be produced by culturing the bacterium of the present invention obtained as described above in a medium to produce and accumulate the L-amino acid in the medium and collecting the L-amino acid from the medium.

To produce an L-amino acid by using the bacterium of the present invention, there can be used ordinary media containing a carbon source, a nitrogen source, inorganic salts and organic trace amount nutrients such as amino acids and vitamins as required in a conventional manner. Either a synthetic medium or a natural medium can be used. Any kinds of carbon source and nitrogen source may be used in the medium so long as they can be utilized by bacterial strains to be cultured.

As the carbon source, saccharides such as glucose, glycerol, fructose, sucrose, maltose, mannose, galactose, starch hydrolysate and molasses are used. Organic acids such as acetic acid and citric acid and alcohols such as ethanol are also used solely or in combination with other carbon sources. Among these, glucose and sucrose are preferred.

As the nitrogen source, there can be used ammonia, ammonium salts such as ammonium sulfate, ammonium carbonate, ammonium chloride, ammonium phosphate and ammonium acetate, nitrates and so forth.

As the organic trace amount nutrients, there can be used amino acids, vitamins, fatty acids and nucleic acids, as well as peptone, casamino acid, yeast extract and soybean protein decomposition product containing these and so forth. When an auxotrophic mutant requiring an amino acid or the like for growth is used, it is preferable to supplement such a required nutrient.

As the inorganic salts, there can be used phosphates, magnesium salts, calcium salts, iron salts, manganese salts and so forth.

As for the culture, although it depends on the type of the bacterium to be used, aeration culture is usually performed while controlling fermentation temperature to 20 to 45° C. and pH to 5 to 9. When pH declines during the culture, calcium carbonate is added, or the culture is neutralized with alkali such as an ammonia gas. By the culture in such a manner for about 10 to 120 hours, a marked amount of L-glutamine is accumulated in a culture broth.

As a method for collecting L-amino acids from the culture broth after completion of the culture, known collection methods, for example, methods utilizing ion exchange resins, precipitation and so forth can be used.

EXAMPLES

Hereafter, the present invention will be explained more specifically with reference to the following examples.

<1> Cloning of Genes of Enzymes Involved in Entner-Doudoroff Pathway

The edd gene and eda gene, which code for enzymes EDD and EDA, respectively, involved in the Entner-Doudoroff pathway, have been cloned from *Escherichia coli, Zymomonas mobilis* and so forth. *Enterobacter agglomerans* taxonomically belongs to the enterobacteria group and is considered to closely relate to *Escherichia coli*. Further, it is known that *Escherichia coli* genes can be expressed in *Enterobacter agglomerans*. Accordingly, it was decided to clone the edd gene and eda gene from *Escherichia coli*.

These two of genes form an operon in *Escherichia coli* (J. Bacteriol., 174 (14): 4638-46, July 1992). Accordingly, edd-F (SEQ ID NO: 1) and eda-R (SEQ ID NO: 2) were designed as primers that could simultaneously amplify both of the genes to amplify a DNA fragment including both of the genes by PCR. PCR was performed by using Pyrobest DNA Polymerase (Takara Shuzo) and consisted of a reaction at 94° C.

for 1 minute, followed by reactions at 94° C. for 30 seconds, 60° C. for 30 seconds and 72° C. for 3 minutes repeated for 30 cycles.

Subsequently, the obtained amplified fragment was completely digested with restriction enzymes SalI and BamHI, ligated with plasmid pMW219 completely digested with restriction enzymes SalI and BamHI and used to transform *Escherichia coli* JM109 (purchased from Takara Shuzo). Five strains of clones containing a fragment having a desired size were selected from the obtained transformants, and plasmids were extracted from these strains.

Each plasmid was introduced into the *Enterobacter agglomerans* AJ13601 strain by the electroporation method (Miller J. H., "A Short Course in Bacterial Genetics; Handbook", Cold Spring Harbor Laboratory Press, U.S.A., p. 279, 1992), and activities of EDD and EDA were measured to select a clone in which the edd gene and eda gene were expressed.

The AJ13601 strain is a bacterial strain obtained as follows. The *Enterobacter agglomerans* AJ13355 strain was isolated from soil as a strain showing resistance to L-glutamic acid under an acidic environment and superior growth rate. Subsequently, a low phlegm-producing mutant strain was derived from the AJ13355 strain, and the αKGDH gene was disrupted to obtain the AJ13356 strain. The AJ13356 strain was deficient in αKGDH activity as a result of disruption of the αKGDH-E1 subunit gene (suca). Subsequently, the AJ13356 strain was introduced with the plasmid RSFCPG having the citrate synthase gene (gltA), phosphoenolpyruvate carboxylase gene (ppc) and glutamate dehydrogenase (gdha) gene of *Escherichia coli* and the plasmid pSTVCB having the gltA gene derived from *Brevibacterium lactofermentum* to obtain SC17sucA/RSFCPG+pSTVCB strain. From this strain, the AJ13601 strain was selected as a bacterial strain showing improved resistance to L-glutamic acid under a low pH environment and the best growth rate (EP 1 078 989 A2).

Strains randomly selected from the transformants introduced with a plasmid including the edd and eda gene fragments as described above were cultured for 15 hours in LBGM9 liquid medium (a medium containing 10 g/L of trypton, 5 g/L of yeast extract, 5 g/L of NaCl and 5 g/L of glucose, added with 1/10 volume of separately sterilized 10×M9 (128 g/L of $Na_2HPO_4 \cdot 7H_2O$, 30 g/L of $KH_2PO_4$, 5 g/L of NaCl, 10 g/L of $NH_4Cl$)) containing tetracycline, chloramphenicol and kanamycin each in an amount of 12.5 mg/L, 25 mg/L or 25 mg/L. The cells were collected from these culture broths by centrifugation, washed twice with 50 mM Tris-HCl buffer (pH 7.6) and 10 mM $MgCl_2$ and then suspended in the same buffer. The cells were disrupted by ultrasonication and centrifuged at 15000 rpm for 30 minutes, and the supernatant was used as a crude enzyme solution.

The activities of EDD and EDA were simultaneously measured by measuring reaction products obtained by two of the enzymes using a photospectrometric technique. That is, 50 mM Tris-HCl (pH 8.0), 10 mM $MgCl_2$, 1 mM EDTA, 1 mM APAD (acetylpyridine adenine dinucleotide), 5 mM $K_2HPO_4$, 20 units of glyceraldehydes-3-phosphate dehydrogenase, 6-phosphogluconic acid and the crude enzyme solution were mixed, and increase of absorbance at 365 nm were measured to measure glyceraldehyde-3-phosphate produced from 6-phosphogluconic acid as a substrate. The same measurement was performed for a strain introduced only with a vector. The results are shown in Table 1.

TABLE 1

| Bacterial strain | Activity (nmol/min/mg protein) |
|---|---|
| PMW219 introduced strain | 1.9 |
| edd/eda enhanced strain 1 | 13.4 |
| edd/eda enhanced strain 2 | 11.5 |
| edd/eda enhanced strain 3 | 13.2 |
| edd/eda enhanced strain 4 | 5.0 |
| edd/eda enhanced strain 5 | 10.9 |

It was confirmed that all the strains had the enhanced activities. In the strain with the highest activities, the activities were enhanced about 7.2 times. The plasmid of this strain was designated as pMW-EDDA.

<2> Production of L-glutamic Acid Using Entner-Doudoroff Pathway Enhanced Strain Then, influence of the enhancement of the Entner-Doudoroff pathway on L-glutamic acid production was examined.

The *Enterobacter agglomerans* AJ13601 strain used in the above section contained two kinds of plasmids, and the strains further introduced with the edd gene and eda gene contained three kinds of plasmids. Therefore, three kinds of agents must be added to the culture, and hence the growth was very poor, i.e., almost no growth was observed in the L-glutamic acid producing culture evaluation system. Therefore, only two kinds of plasmids were used by introducing a citrate synthase (also referred to as "CS", hereinafter) gene of *Brevibacterium lactofermentum*, the edd gene and eda gene into one plasmid.

Of the vector pSTV28 used for the construction of the plasmid pSTVCB containing the CS gene of *Brevibacterium lactofermentum* and the vector pMW219 used for cloning of the edd gene and eda gene, the former shows a higher copy number. It was considered that, while the CS gene of *Brevibacterium lactofermentum* is enhanced by the pSTV28 vector in the AJ13601 strain, it was necessary to increase the expression amount for introducing this gene by using pMW219. Therefore, a gene of which promoter region in the CS gene was replaced with that of the CS gene of *Escherichia coli* was constructed.

Specifically, the promoter region in the CS gene was amplified by using primers GLTES1 (SEQ ID NO: 3) and GLTEB0 (SEQ ID NO: 4) and chromosome of the *Escherichia coli* W3110 strain as a template. Further, a fragment containing the ORF region of the CS gene was amplified by using primers GLTBB0 (SEQ ID NO: 5) and GLTBA1 (SEQ ID NO: 6) and chromosome of the *Brevibacterium lactofermentum* 2256 strain as a template. Crossover PCR was performed by using both of the fragments as templates and primers GLTES2 (SEQ ID NO: 7) and GLTBA2 (SEQ ID NO: 8) to obtain a target fragment. This fragment was digested with restriction enzymes SmaI and HindIII and introduced into the same site of pSTV28 to obtain pSTV-$C^B$(*). This plasmid was digested with KpnI and HindIII, and a fusion gene fragment containing the promoter of the CS gene of *Escherichia coli* and the coding region of the CS gene of the *Brevibacterium lactofermentum* was collected and blunt-ended with T4 DNA polymerase. This fusion gene fragment was introduced into the SmaI site of pMW219 to obtain pMW-$C^B$(*). Further, pMW-EDDA was treated with BamHI and ligated with the above fusion gene fragment, and the ligation product was blunt-ended with T4 DNA polymerase to obtain pMW-$C^B$(*)·ED.

Subsequently, AJ13601 was shaken overnight in LBGM9 liquid medium at 31.5° C., suitably diluted so that 100 to 200 colonies should be obtained per plate and applied on an LBGM9 plate containing 12.5 mg/L of tetracycline. The emerged colonies were replicated on an LBGM9 plate containing 12.5 mg/L of tetracycline and 25 mg/L of chloramphenicol, and a strain that became chloramphenicol sensitive was collected and designated as G106S. The G106S strain contained only RSFCPG and was deficient in pSTVCB. Strains obtained by introducing pMW-$C^B$(*) or pMW-$C^B$(*)·ED into this strain were designated as G106S pMW·$C^B$(*) and G106S pMW-$C^B$(*)·ED, respectively.

To evaluate L-glutamic acid producing ability of these strains, culture evaluation using a jar fermenter was carried out for them. The used medium was 300 ml of a medium containing 50 g/L of sucrose, 0.4 g/L of $MgSO_4$, 0.1 mL/L of GD-113 (defoaming agent), 4 g/L of $(NH_4)_2SO_4$, 2 g/L of $KH_2PO_4$, 4 g/L of yeast extract, 10 mg/L of $FeSO_4.7H_2O$, 10 mg/L of $MnSO_4.4-5H_2O$, 0.4 g/L of L-lysine, 0.4 g/L of DL-methionine, 0.4 g/L of diaminopimelic acid, 12.5 mg/L of tetracycline and 25 mg/L of chloramphenicol. The culture was performed with aeration of 1/1 VVM, stirring at 1300 rpm and pH 6.0 controlled with ammonia until sucrose was consumed. Changes with time in absorbance at 660 nm and the production amounts of L-glutamic acid in the media are shown in FIG. 1. Further, the final production amounts of L-glutamic acid are shown in Table 2.

TABLE 2

|  | OD 620 nm (×1/101) | Culture time (h) | L-glutamic acid (g/L) |
|---|---|---|---|
| G106S pMW•$C^B$(*) | 0.334 | 12 | 30.4 |
| G106S pMW-$C^B$(*)•ED | 0.258 | 16 | 36.8 |

It was revealed that the L-glutamic acid producing ability could be improved by enhancing the Entner-Doudoroff pathway, although the culture was delayed.

<3> Investigation of Production of Acetoin and 2,3-butanediol by Entner-Doudoroff Pathway Enhanced Strain The aforementioned G106S pMW.$C^B$(*) and G106S pMW-$C^B$(*)·ED strains were cultured in the same manner as in the evaluation for the L-glutamic acid producing ability in <2>, and the amounts of acetoin and 2,3-butanediol in the medium and cells were measured in a time course. The measurement was performed by gas chromatography (Shimadzu Corporation, GC-1700A) under the following conditions.

Column used: VARIAN PORAPLOTQ PLOT FS25X32 (0.32 mm×25 M)

Temperature: Vaporization room: 250° C., column: 240° C., FID: 250° C.

Column inlet pressure: 180 kPa

Carrier gas flow rate: 1.6062 ml/min

Figure 2:
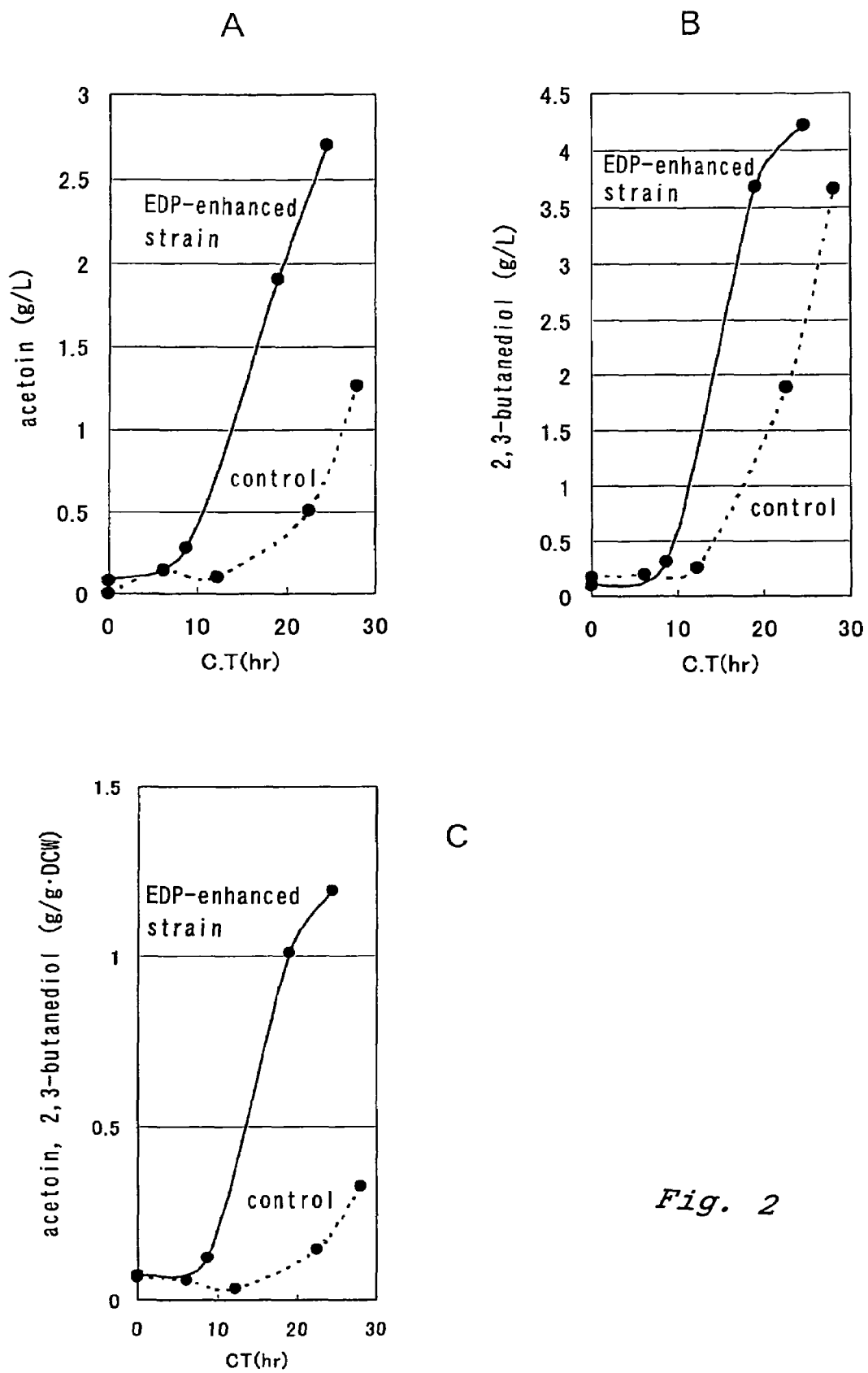
FIG. 2 shows the amounts of acetoin and 2,3-butanediol produced by a strain in which the edd gene and eda gene are enhanced: (A) amount of acetoin in a medium, (B) amount of 2,3-butanediol in a medium, and (C) total amount of produced acetoin and 2,3-butanediol per unit bacterial cells (weight per unit dry cell weight).

The results are shown in FIG. 2A (acetoin amount in the medium), FIG. 2B (2,3-butanediol amount in the medium) and FIG. 2C (total amount of produced acetoin and 2,3-butanediol per unit cells). It was revealed that production of acetoin and 2,3-butanediol was increased by enhancing the Entner-Doudoroff pathway.

What is claimed is:

1. A method for producing an L-amino acid comprising culturing a microorganism having an ability to produce an L-amino acid in a medium to produce and accumulate the L-amino acid in the medium and collecting the L-amino acid from the medium, wherein the microorganism is a Gram-negative bacterium having the Entner-Doudoroff pathway and which has been modified so that 6-phosphogluconate dehydratase activity or 2-keto-3-deoxy-6-phosphogluconate aldolase activity, or activities of the both are enhanced, and the L-amino acid is selected from L-amino acids produced by a biosynthetic pathway utilizing pyruvic acid as an intermediate, wherein the 6-phosphogluconate dehydratase is encoded by edd gene and the 2-keto-3-deoxy-6-phosphogluconate aldolase is encoded by eda gene.

2. The method according to claim 1, wherein the edd gene or the eda gene are derived from *Escherichia coli*.

3. The method according to claim 1, wherein the bacterium is an enterobacterium.

4. The method according to claim 3, wherein the bacterium is belonging to the genus *Enterobacter*.

5. The method according to claim 1, wherein the 6-phosphogluconate dehydratese activity or 2-keto-3-deoxy-6-phosphogluconate aldolase activity is enhanced by increasing copy number of a gene coding for 6-phosphogluconate dehydratase or 2-keto-3-deoxy-6-phosphogluconate aldolase or modifying an expression regulatory sequence of the gene so that expression of the gene is enhanced in a cell of the bacterium.

6. The method according to claim 1, wherein the edd gene or the eda gene is a gene which is included in the DNA fragment obtainable by PCR using chromosomal DNA of *Escherichia coli* as a template and the primers of SEQ ID NOs: 1 and 2.

7. The method according to claim 1, wherein the edd gene or the eda gene is hybridizable with the nucleotide sequence of GenBank accession number L20897 under the condition of 1×SSC, 0.1% SDS, at 60° C.

8. The method according to claim 1, wherein the L-amino acid is L-glutamic acid or an L-amino acid produced by a biosynthetic pathway utilizing L-glutamic acid as an intermediate or an amino group donor.

9. The method according to claim 1, wherein the L-amino acid is selected from L-glutamic acid, L-arginine, L-glutamine, L-proline, L-leucine, L-isoleucine, L-valine and L-alanine.

10. The method according to claim 9, wherein the L-amino acid is L-glutamic acid.

* * * * *

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: Synthetic DNA

<400> SEQUENCE: 1
cgctagtcga ccaattttta cactttcagg cctcg                              35

<210> SEQ ID NO 2
<211> LENGTH: 35
<212> TYPE: DNA
<213> ORGANISM: Artificial Sequence
<220> FEATURE:
<223> OTHER INFORMATION: Synthetic DNA

<400> SEQUENCE: 2 ggggggatc cagtcagaat gtcacgtttg ataat                               35

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
cccccgggtc tgttacctgc agacgtcg                                      28
```

<210> SEQ ID NO 4
<211> LENGTH: 42
<212> TYPE: DNA
<213> ORGANISM: Artificial Sequence
<220> FEATURE:
<223> OTHER INFORMATION: Synthetic DNA

<400> SEQUENCE: 4
acgcacgata tccctttcaa acatttaagg tctccttagc gc           42

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
gtttgaaagg gatatcgtgg ct                                 22

<210> SEQ ID NO 6
<211> LENGTH: 27
<212> TYPE: DNA
<213> ORGANISM: Artificial Sequence
<220> FEATURE:
<223> OTHER INFORMATION: Synthetic DNA

<400> SEQUENCE: 6
aaaagcttat cgacgctccc ctcccca                            27

<210> SEQ ID NO 7
<211> LENGTH: 30
<212> TYPE: DNA
<213> ORGANISM: Artificial Sequence
<220> FEATURE:
<223> OTHER INFORMATION: Synthetic DNA

<400> SEQUENCE: 7
cccccgggat ttccttcctc cggtctgctt                         30

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
taaagcttgg tcagggcgtt ggcggtggcg                         30